United States Patent [19]

Metters

[11] Patent Number: 4,829,995
[45] Date of Patent: May 16, 1989

[54] FLUID BARRIER FOR MEDICAL DRESSING

[75] Inventor: John R. Metters, Hingham, Mass.

[73] Assignee: Aegis Medical Corporation, Weymouth, Mass.

[21] Appl. No.: 93,502

[22] Filed: Sep. 4, 1987

[51] Int. Cl.⁴ ............................................. A61L 15/00
[52] U.S. Cl. ..................... 128/156; 128/155; 128/846; 604/304; 604/289; 428/351; 401/207
[58] Field of Search .................. 128/132 R, 155, 156, 128/355; 206/438, 439, 440, 441; 604/896, 897, 289; 24/DIG. 11; 428/351, 354; 401/207; 15/104.94, 209 R, 209 E

[56] References Cited

U.S. PATENT DOCUMENTS

| Re. 31,886 | 5/1985 | Hodgson | 428/40 |
|---|---|---|---|
| 481,735 | 8/1892 | Pidgin | 281/38 |
| 706,250 | 8/1902 | Moller | 128/154 |
| 1,524,399 | 1/1925 | Krueger | 229/52 A |
| 1,671,825 | 5/1928 | Johnson | 206/440 |
| 2,071,961 | 2/1937 | Landsiedel | 206/57 |
| 2,529,060 | 11/1950 | Trillich | 117/68.5 |
| 2,649,199 | 8/1953 | Werman | 206/63.2 |
| 2,755,800 | 7/1956 | Thompson | 128/155 |
| 2,904,041 | 9/1959 | Brown | 128/132 |
| 3,077,683 | 2/1963 | Jones | 40/2 |
| 3,094,323 | 6/1963 | Catania | 271/33 |
| 3,128,072 | 4/1964 | Shibata | 248/29 |
| 3,486,504 | 12/1969 | Austin, Jr. | 604/289 |
| 3,677,225 | 7/1972 | Czirely | 128/132 |
| 4,022,203 | 5/1977 | Ackley | 128/156 |
| 4,121,386 | 10/1978 | Perez | 15/209 R |
| 4,176,664 | 12/1979 | Kalish | 604/290 |
| 4,285,338 | 8/1981 | Lemelson | 128/155 |
| 4,297,995 | 11/1981 | Golub | 128/156 |
| 4,650,705 | 3/1987 | Ghodsian | 128/155 |
| 4,706,661 | 11/1987 | Barrett | 128/155 |
| 4,754,750 | 7/1988 | Imonti | 128/156 |

FOREIGN PATENT DOCUMENTS 8607252 12/1986 World Int. Prop. O. .......... 128/156

Primary Examiner—Richard J. Apley
Assistant Examiner—Paul Prebilic
Attorney, Agent, or Firm—Lahive & Cockfield

[57] ABSTRACT

Disclosed is a barrier for medical dressings which is impervious to blood or other body fluids. The barrier may be joined or pre-attached to the top surface of a medical dressing. The dressing may then be handled by the barrier and applied to a wound. The barrier prevents blood and other body fluids from penetrating the dressing and contacting a health care worker or other individual who may be treating the patient.

16 Claims, 1 Drawing Sheet

FLUID BARRIER FOR MEDICAL DRESSING

BACKGROUND OF THE INVENTION

The present invention is directed to fluid barriers for medical dressings. More particularly, the invention is directed to a medical dressing having an outer barrier which is impervious to body fluids.

Recently there has been concern over the risk of contacting infectuous diseases such as AIDS through contact with tainted blood or other body fluids. Doctors, nurses, medical technicians and other persons in the health care field form a group which faces a particularly high risk of contacting such diseases. It is known, for example, that the AIDS virus, as well as other harmful bacteria and viruses, may be transmitted through contact with medical dressings, syringes, and the like, which bear contaminated blood or body fluids. Health care professionals may contact life-threatening diseases through contact with such items.

The risk of contacting potentially fatal diseases can be greatly reduced by providing bandages and dressings with a protective barrier impervious to blood and body fluids. Conventional gauze bandages and other dressings do not lessen the risk of infection posed to health care workers. When such absorbent dressings are placed over as wound, blood often penetrates the dressing. Health care workers treating a patient may then be exposed to bacteria and viruses through contact with the soiled dressing. Thus, there exists a need to provide additional protection to health care workers by limiting their potential for exposure to such bacteria and viruses.

Accordingly, it is an object of the present invention to provide a medical dressing having one side which is impervious to the passage of blood and other body fluids. Another object of the invention is to provide a fluid-impermeable material which may be adhesively secured to a conventional medical dressing. A further object of the invention is to provide a dressing or apparatus which is easily and safely handled. Other objects of the invention will be apparent to those of ordinary skill in the art upon reading the present disclosure.

SUMMARY OF THE INVENTION

The present invention comprises a fluid-impermeable barrier material which may be adhesively secured to a conventional medical dressing, such as a bandage or gauze pad, to form a shield which protects a health care worker from exposure to blood or body fluids if they penetrate the dressing. The barrier comprises a substrate which may be made of plastic, paper or other suitable materials impervious t fluids. One side of the substrate contains an adhesive coating, which is likewise substantially impermeable, and may be used to affix a bandage or dressing to the barrier material. A strip of foil may be disposed between the substrate and the adhesive layer to form a more effective barrier. In addition, a top side of the substrate may include an upwardly protruding tab, which may be integral with the barrier material, to provide a means for easily handling the dressing.

In one embodiment, a dressing may be adhered to the barrier once the adhesive layer is exposed. With the dressing firmly secured to a barrier a health care worker may grasp the barrier material and apply the dressing to a wound. The barrier will prevent blood and body fluids from coming into contact with skin of the health care worker. When the dressing is no longer needed it may be removed by grasping the tab and discarded.

In another embodiment of the invention, dressings and bandages may be manufactured with a pre-secured barrier.

DETAILED DESCRIPTION OF THE INVENTION

Figure 1:
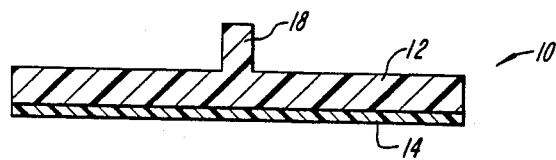
FIG. 1 is a schematic cross section of one embodiment of the medical dressing barrier of the present invention.

As shown in FIG. 1, the medical dressing barrier 10 of the present invention includes a fluid-impermeable substrate material 12 and an adhesive layer 14. In another embodiment of the invention, illustrated in FIG. 2, a foil strip 16 is disposed between the substrate material 12 and the adhesive layer 14. In addition, the embodiments of FIGS. 1 and 2 each include a tab means 18 which protrudes from a top surface of the substrate material. Tab means 18, which may be integral with the substrate, functions as a handle which facilitates convenient and safe handling of the dressing barrier 10.

Figure 2:
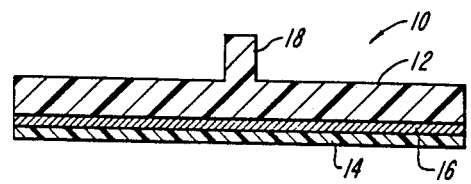
FIG. 2 is a schematic cross section of another embodiment of the medical dressing barrier of the present invention.
Figure 3:
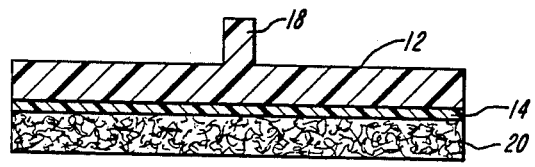
FIG. 3 is a schematic cross section of the medical dressing barrier of FIG. 1 having a medical dressing attached thereto.
Figure 4:
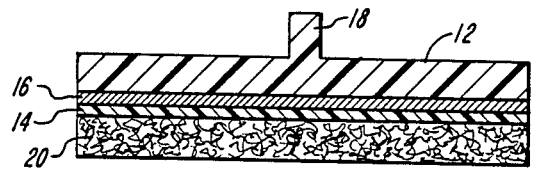
FIG. 4 is a schematic cross section of the medical dressing barrier of FIG. 2 having a medical dressing affixed thereto.
Figure 4A:
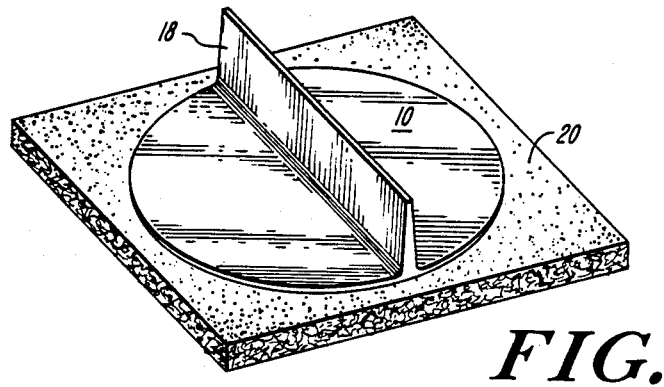
FIG. 4A is a perspective view of a medical dressing barrier of the present invention affixed to a medical dressing.

FIG. 3 illustrates another embodiment of the invention whereby the dressing barrier 10 of FIG. 1 has a dressing 20 adhered thereto. FIGS. 4 and 4A illustrate the barrier 10 of FIG. 2 with a dressing 20 adhered thereto. The embodiments of FIGS. 3, 4 and 4A may either be manufactured in such a way that the dressing 20 is pre-secured to the barrier 10, or the barrier 10 may be manufactured separately and subsequently joined to a dressing 20 prior to use.

The substrate material 12 of the present invention may be constructed from virtually any material of suitable strength which is acceptable for pharmaceutical and medical applications. In a preferred embodiment, the substrate comprises a flexible material. The substrate should also be of such a quality that it is impervious to blood and other body fluids. In addition, the substrate should have affixed to one of its sides an adhesive material, such as an acrylic adhesive, which is suitable for pharmaceutical and medical applications. The medical dressing material 20 the present invention may be of any type of bandaging, gauze or dressing material known in the art.

In a preferred embodiment of the invention, the substrate material is manufactured from 50 pound paper known as Silverback Pharmaceutical Paper, manufactured and sold by Fasson Company. This material includes a permanent pressure sensitive acrylic-based adhesive 14, known as S-727, which is affixed to the bottom of substrate 12. The preferred substrate material includes a thin layer of foil 16 which is disposed between the substrate and the adhesive in order to provide additional protection from fluid leakage. In this embodiment, it is believed that the medical dressing barrier is totally impervious to blood and other body fluids.

Other preferred substrate materials which are equally useful include the 50 pound pharmaceutical Hi-gloss Facestock and 50 pound Pharmaceutical Lithofacestock, both of which are manufactured and sold by Fasson Company. While these substrate materials lack a foil layer 16, they both provide excellent protection against the passage of fluids.

In one embodiment, the medical dressing barriers of FIGS. 1 and 2 may be sold separately and subsequently affixed to a medical dressing just prior to use of the dressing. In this embodiment, a health care worker would remove a protective strip (not shown) covering the adhesive layer and then handle the barrier 10 by tab 18 to secure the barrier 10 to a bandage or dressing of a corresponding size. The adhesive layer 14 would enable the barrier 10 to firmly and securely grasp and retain the dressing. The dressing could then be applied to the wound while pressure is applied through the barrier 10. The dressing may be safely removed from the patient by grasping the barrier 10 (which still retains the dressing) through tab 18 and disposing the entire unit. In this way, the health care worker is not exposed to any blood or bodily fluid which may have penetrated the dressing.

In another embodiment of the invention, the medical dressing barrier 10 my be provided with a pre-attached dressing or bandage of a corresponding size, as shown in FIGS. 3, 4 and 4A. In this embodiment, the dressing can simply be applied to a wound by grasping the barrier 10 through tab 18.

FIG. 4A illustrates the medical barrier 10 adhered to a dressing material 20. The entire unit may be handled by tab 18.

It is understood that the apparatus of the present invention may be provided in a variety of shapes and sizes depending on the requirements of a particular application. In addition, other variations or modifications of the present invention may be made by one having ordinary skill in the art without departing from the scope of the present invention.

What is claimed is:

1. A medical dressing protective barrier apparatus, comprising:
   a planar substrate means, substantially fluid impermeable across the entire plane of its surface;
   an adhesive material applied to entirely cover a first, bottom surface of the substrate means said adhesive material being re-usably attachable to a bandage or dressing; and
   an upwardly protruding tab means which forms part of a second, upper surface of the substrate means for facilitating handling of the apparatus.

2. The apparatus of claim 1 wherein said substrate material comprises a paper material suitable for use in pharmaceutical or medical applications.

3. The apparatus of claim 1 wherein said substrate material comprises a polymeric material suitable for use in pharmaceutical or medical applications.

4. The apparatus of claim 1 wherein said adhesive material comprises a material suitable for use in pharmaceutical or medical applications.

5. The apparatus of claim 4 wherein said adhesive is an acrylic material.

6. The apparatus of claim 5 wherein said adhesive is a permanent, pressure sensitive adhesive.

7. The apparatus of claim 4 further comprising a removable strip covering and protecting said adhesive layer.

8. The apparatus of claim 7 wherein said adhesive layer is adapted to permanently secure a medical dressing to the substrate means.

9. The apparatus of claim 4 wherein said tab means protrudes upwardly from said substrate means.

10. The apparatus of claim 4 wherein said tab means is integral with said substrate means.

11. The apparatus of claim 4 wherein said tab means is permanently secured to the substrate means.

12. The apparatus of claim 4 further comprising a medical dressing adhesively secured to the first surface of the substrate means.

13. The apparatus of claim 4 further comprising a strip of foil disposed between the substrate and the adhesive material.

14. A medical dressing apparatus, comprising:
   an absorbent dressing means for covering a wound;
   a planar substrate means, substantially fluid impermeable across the entire plane of its surface having an adhesive layer applied to a first, bottom surface thereof, the adhesive layer permanently securing the dressing means to the substrate; and
   tab means which forms part of a second, upper surface of the substrate and portrudes upwardly therefrom for facilitating handling of the apparatus.

15. The apparatus of claim 14 further comprising a foil strip means disposed between the substrate means and the adhesive means.

16. The apparatus of claim 15 wherein said foil strip means is impermeable to fluids.

* * * * *